United States Patent
Pitcher et al.

(10) Patent No.: US 10,272,130 B1
(45) Date of Patent: Apr. 30, 2019

(54) ORAL ANAEROBIC GLUTATHIONE SUPPLEMENT IN LIPOSOME SUSPENSION

(71) Applicants: Stephen N. Pitcher, Alpine, UT (US); Danny Clinton Purser, Provo, UT (US)

(72) Inventors: Stephen N. Pitcher, Alpine, UT (US); Danny Clinton Purser, Provo, UT (US)

( * ) Notice: Subject to any disclaimer, the term of this patent is extended or adjusted under 35 U.S.C. 154(b) by 0 days.

(21) Appl. No.: 15/955,608

(22) Filed: Apr. 17, 2018

Related U.S. Application Data

(60) Provisional application No. 62/460,725, filed on Feb. 17, 2017.

(51) Int. Cl.

| | |
|---|---|
| *A61K 47/24* | (2006.01) |
| *A61K 38/06* | (2006.01) |
| *A61K 9/127* | (2006.01) |
| *A61K 9/00* | (2006.01) |
| *A61P 7/00* | (2006.01) |
| *A61K 47/12* | (2006.01) |
| *A61K 47/46* | (2006.01) |
| *A61K 47/10* | (2017.01) |
| *A61K 49/18* | (2006.01) |

(52) U.S. Cl.
CPC .......... *A61K 38/063* (2013.01); *A61K 9/0019* (2013.01); *A61K 9/1271* (2013.01); *A61K 47/10* (2013.01); *A61K 47/12* (2013.01); *A61K 47/46* (2013.01); *A61P 7/00* (2018.01); *A61K 49/1839* (2013.01)

(58) Field of Classification Search
CPC .. A61K 2300/00; A61K 38/063; A61K 9/127; A23V 2250/31
See application file for complete search history.

(56) References Cited

U.S. PATENT DOCUMENTS

| | | | | |
|---|---|---|---|---|
| 6,835,811 B1* | 12/2004 | Harbin | ..................... | A61K 9/08 530/332 |
| 2001/0046471 A1* | 11/2001 | Marek | ..................... | A61B 5/015 424/9.1 |
| 2014/0023696 A1* | 1/2014 | Guilford | .............. | A61K 38/063 424/450 |
| 2016/0081327 A1* | 3/2016 | Menon | ................. | A01N 1/0226 435/1.1 |

OTHER PUBLICATIONS

Lecithin. Catalog # 1044. Matreya LLC. https://www.matreya.com/BVModules/ProductTemplates/Matreya/Product.aspx?productid=1044[Nov. 11, 2018 11:42:24 PM]. (Year: 2018).*
Beeh et al. Glutathione deficiency of the lower respiratory tract in patients with idiopathic pulmonary fibrosis. Eur Respir J. 2002; 19: 1119-1123. (Year: 2002).*
Pure Water. All Distilled Water Is Not the Same. https://mypurewater.com/blog/2011/02/14/all-distilled-water-is-not-the-same/[Nov. 30, 2018 12:46:17 PM] (Year: 2011).*

* cited by examiner

*Primary Examiner* — Marcela M Cordero Garcia
*Assistant Examiner* — Jia-Hai Lee
(74) *Attorney, Agent, or Firm* — Terrence J. Edwards; TechLaw Ventures, PLLC

(57) ABSTRACT

The disclosure relates to compositions, methods and systems for treating cellular oxidative stress in a user. A composition of the disclosure includes an effective amount of reduced glutathione for reducing oxidative stress in the user and a deoxygenated water solvent. The composition is encapsulated in a phospholipid liposome structure and packaged and stored in an airless dispenser configured to maintain an anaerobic environment.

23 Claims, 12 Drawing Sheets

1200

> Providing A Composition To The User, Wherein The Composition Comprises:
>
> An Effective Amount Of Reduced Glutathione For Reducing Oxidative Stress In The User; And
>
> A Deoxygenated Water Solvent.
>
> 1202

> Providing A Composition To The User, Wherein The Composition Comprises:
>
> An Effective Amount Of Reduced Glutathione For Reducing Oxidative Stress In The User;
>
> A Deoxygenated Water Solvent;
>
> An Effective Amount Of One Or More Preservatives; And
>
> An Effective Amount Of One Or More Natural Flavoring Components For Improving An Overall Flavor Of The Composition;
>
> Wherein The Reduced Glutathione Comprises From About 8% To About 14% By Weight Of The Total Composition;
>
> Wherein The Reduced Glutathione Comprises A Purity From About 98% To About 99.9% Purity;
>
> Wherein The Composition Is Encapsulated In A Phospholipid Liposome Structure; And
>
> Wherein The Composition Is Packaged In An Airless Dispenser Configured To Maintain An Anaerobic Environment.
>
> 1302

FIG. 13

ORAL ANAEROBIC GLUTATHIONE SUPPLEMENT IN LIPOSOME SUSPENSION

CROSS-REFERENCE TO RELATED APPLICATIONS

This application claims the benefit under 35 U.S.C. § 119(e) of U.S. Provisional Application No. 62/460,725 filed Feb. 17, 2017, which is hereby incorporated by reference herein in its entirety.

STATEMENT REGARDING FEDERALLY SPONSORED RESEARCH OR DEVELOPMENT

Not Applicable.

BACKGROUND

The disclosure relates to compositions, methods and systems for improving free radical levels in a user and/or for the treatment of oxidative stress in a user. The compositions, methods, and systems of the disclosure may also be applicable in the treatment or support of the body's natural detoxification process and/or the treatment or support of the body's natural defense systems for combatting viruses, bacteria, heavy metal toxicity, radiation, certain medications, the process of aging, and the like.

The present disclosure relates to a bio-effective nutraceutical composition. Specifically, the disclosure relates to a composition comprising reduced glutathione (GSH) manufactured to be substantially anaerobic and remaining in a reduced glutathione state at composition.

What is needed are compositions, methods, and systems that are efficient for reducing free radical levels in a user and alleviating oxidative stress in the user. As will be seen, the disclosure provides such compositions, methods, and systems that can treat oxidative stress and improving the body's natural detoxification process and natural defense systems in an effective and elegant manner.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with respect to the following description and accompanying drawing where:

FIG. 12 illustrates a schematic block diagram of a method for reducing oxidative stress in a user; and FIG. 13 illustrates a schematic block diagram of a method for reducing oxidative stress in a user.

DETAILED DESCRIPTION

Figure 1:
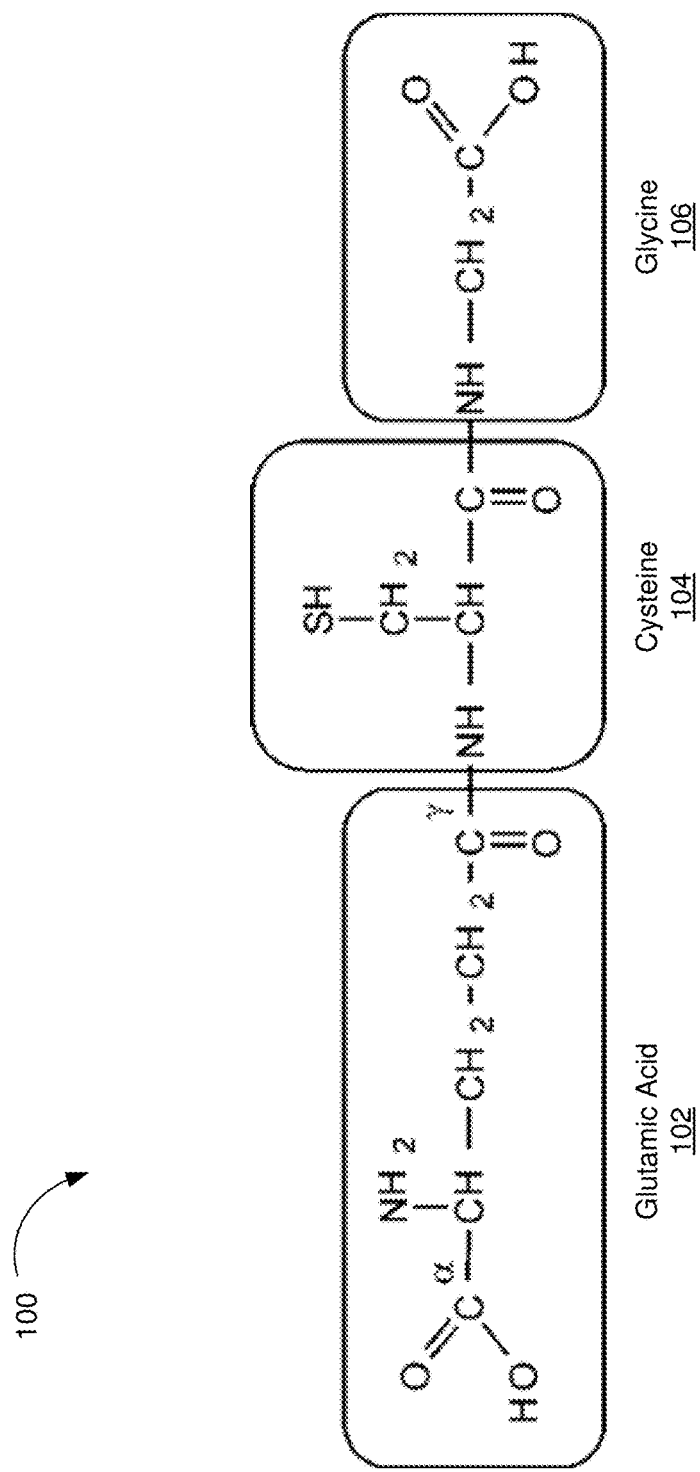
FIG. 1 illustrates the chemical structure of reduced glutathione (GSH) according to one implementation consistent with the teachings and principles of the disclosure.

The disclosure extends to compositions, methods, and systems for alleviating oxidative stress in a user and/or the reducing the levels of damaging free radicals in the user that may be accumulated due to viruses, bacteria, heavy metal toxicity, radiation, certain medications, the process of aging, and the like. The disclosure further extends to the anaerobic manufacture, packaging, and delivery of therapeutic amounts of bio-effective reduced glutathione (GSH).

The disclosure extends to a highly bio-active composition for reducing oxidative stress in a user. The composition includes reduced glutathione and a deoxygenated water solvent, and the composition may be encapsulated in a phospholipid liposome structure to provide effective delivery to the user. The composition provides unexpectedly good results in maintaining reduced glutathione that is effective for alleviating cellular oxidative stress in a user and/or reducing a level of free radicals in the user's body. Compared with compositions known in the art that purport to provide reduced glutathione, the composition of the present disclosure provides unexpectedly good results in preventing the oxidation of reduced glutathione (GSH) to oxidized glutathione (GSSG) that is commonly found in purported GSH supplements known in the art. The composition provides unexpectedly good results in passing reduced glutathione through the mucosa membrane of a user directly into the user's bloodstream such that the user may receive effective relief from cellular oxidative stress and may reduce the levels of free radicals in the body. The composition of the disclosure provides unexpectedly good results in increasing levels of reduced glutathione in a user's blood serum over short-term and long-term periods. The composition further provides unexpectedly good results in improving the ratio of reduced glutathione to oxidized glutathione in a user's blood serum over short-term and long-term periods.

The disclosure further extends to the anaerobic manufacture and packaging of a composition for reducing oxidative stress in a user. The composition provides reduced glutathione in a deoxygenated water solvent, wherein all or nearly all oxygen gas ($O_2$) commonly found in water has been removed. The composition is encapsulated in a phospholipid liposome structure that provides some protection against oxidation of the reduced glutathione. The composition is further packaged in an airless dispenser. The composition provides high bio-activity in alleviating cellular oxidative stress in a user and reducing levels of free radicals in a user's body.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified ingredients, materials or steps and those that do not materially affect the basic and novel characteristic or characteristics of the claimed disclosure.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

Unless defined otherwise, all technical and scientific terms used herein have the same meanings as commonly understood by one of ordinary skill in the art to which this disclosure pertains and belongs.

Oxidative stress, or high levels of free radicals in the body, is responsible for numerous health issues and is virtually impossible to avoid. Oxidative stress reflects an imbalance between the systemic manifestation of reactive oxygen species and the body's ability to readily detoxify the reactive intermediates or repair the resulting damage. Disturbances in the body's normal redox state of cells can cause toxic effects through the production of peroxides and free radicals that damage all components of a cell, including proteins, lipids, and DNA. Oxidative stress from oxidative metabolism causes base damage as well as strand breaks in DNA. Further, some reactive oxidative species act as cellular messengers in redox signaling. Thus, oxidative stress may cause disruptions in the body's normal mechanisms of cellular signaling. In humans, oxidative stress is thought to be involved in the development of attention deficit hyperactivity disorder, cancer, Parkinson's disease, Lafora disease, Alzheimer's disease, atherosclerosis, heart failure, myocardial infarction, fragile X syndrome, sickle-cell disease, licen planus, vitiligo, autism, infection, chronic fatigue syndrome, and depression, among other.

Chemically, oxidative stress is associated with increased production of oxidizing species or a significant decrease in the effectiveness of antioxidant defenses, such as glutathione. Reduced glutathione (GSH) is often referred to as the body's master antioxidant. Glutathione is composed of three amino acids, including cysteine, glycine, and glutamine, and glutathione can be found in virtually every cell of the body. The highest concentration of glutathione is typically found in the liver where it serves a critical function in the body's natural detoxification process. This natural detoxification process is important for treating oxidative stress in the body and avoiding the production of damaging peroxides and free radicals.

Glutathione is an important component of the body's natural defense system. Glutathione can be depleted by compositions or processes that are associated with free-radical damage, including for example, viruses, bacteria, heavy metal toxicity, radiation, certain medications, and the process of aging. The depletion of glutathione is associated with lower immune function, increased vulnerability to infection, and a reduction in the liver's ability to detoxify the body. As the generation of free radicals exceeds the body's ability to neutralize and eliminate them, oxidative stress occurs. A primary function of glutathione is to alleviate oxidative stress.

Reduced glutathione is under tight homeostatic control both intracellularly and extracellularly. A dynamic balance is maintained between the synthesis of reduced glutathione, its recycling from oxidized glutathione, and its utilization.

Reduced glutathione is utilized as a cofactor by multiple peroxidase enzymes to detoxify peroxides that are generated by oxygen radical attack on biological molecules. Reduced glutathione is further utilized as a cofactor by transhydrogenases to reduce oxidized centers on DNA, proteins, and other biomolecules. Reduced glutathione is further utilized as a cofactor by glutathione S-transferases (hereinafter "GST") to conjugate reduced glutathione with endogenous substances (e.g. estrogens), exogenous electrophiles (e.g. arene oxides, unsaturated carbonyls, and organic halides), and diverse xenobiotics. Low GST activity may increase risk for disease, and paradoxically, some reduced glutathione conjugates can also be toxic.

Reduced glutathione can be depleted by direct attack by free radicals and other oxidative agents. The homeostatic glutathione redox cycle attempts to keep reduced glutathione repleted as it is being consumed. Amounts available from foods are limited (less than 150 mg/day), and oxidative depletion can outpace synthesis.

The liver is the largest reservoir of reduced glutathione. The parenchymal cells synthesize reduced glutathione for P450 conjugation and numerous other metabolic requirements, then export reduced glutathione as a systemic source of SH-reducing power. Reduced glutathione is carried in the bile to the intestinal luminal compartment. Epithelial tissues of the kidney tubules, intestinal lining, and lungs have substantial P450 activity and a modest capacity to export reduced glutathione. However, it will be appreciated that glutathione exists in the intracellular and extracellular spaces of all cells and is present throughout the body.

Equivalents of reduced glutathione circulate in the blood predominately as cystine (i.e., the oxidized and more stable form of cysteine.) Cells import cystine from the blood, reconvert it to cysteine, and form it to synthesize reduced glutathione. Conversely, inside the cell, reduced glutathione assists in re-reducing oxidized forms of other antioxidants such as ascorbate and alpha-tocopherol.

Reduced glutathione is an important cell protectant; it directly quenches reactive hydroxyl free radicals, other oxygen-centered free radicals, and radical centers on DNA and other biomolecules. Reduced glutathione is a primary protectant of the skin, lens, cornea, and retina against radiation damage and other biochemical foundations of P450 detoxification in the liver, kidneys, lungs, intestinal, epithelia, and other organs.

Reduced glutathione is the essential cofactor for many enzymes that require thiol-reducing equivalents, and it helps keep redox-sensitive active sites on enzymes in the necessary reduced state. Higher-order thiol cell systems, the metallothioneins, thioredoxins, and other redox regulator proteins are ultimately regulated by the levels of reduced glutathione, and the ratio of reduced glutathione to oxidized glutathione. The balance of reduced and oxidized glutathione is crucial to homeostasis in the body, to stabilizing the cellular biomolecular spectrum, and to facilitating cellular performance and survival. Reduced glutathione and its metabolites interface with energetics and neurotransmitter syntheses through several prominent metabolic pathways. Reduced glutathione availability down-regulates the pro-inflammatory potential of leukotrienes and other eicosanoids. Recently discovered S-nitroso metabolites, generated in vivo from reduced glutathione and nitric oxide (NO), further diversify the impact of reduced glutathione on the body's metabolism.

According to the present disclosure, a reduced glutathione supplement may be manufactured in an anaerobic environment using one or more non-reactive gasses to ensure the maintenance of the reduced form, rather than the oxidized form, of glutathione. Additionally, de-oxygenated water may be used during the manufacturing process and as a carrier for the supplement. By using de-oxygenated water, very little of the oxygen is available in the water to convert the reduced glutathione to oxidized glutathione.

In an embodiment of the disclosure, a composition for reducing oxidative stress in a user is disclosed. The composition includes an effective amount of reduced glutathione for reducing oxidative stress in the user, and a deoxygenated water solvent. In an embodiment, the composition is encapsulated in a phospholipid liposome structure. In an embodiment, the composition is packaged in an airless dispenser configured to maintain an anaerobic environment.

In a further embodiment of the disclosure, a method of reducing oxidative stress in a user is disclosed. The method includes providing a composition to the user, wherein the composition comprises an effective amount of reduced glutathione for reducing oxidative stress in the user and a deoxygenated water solvent. In an embodiment, the composition is encapsulated in a phospholipid liposome structure and the composition is packaged in an airless dispenser configured to maintain an anaerobic environment.

In a further embodiment of the disclosure, a method for manufacturing a composition for reducing oxidative stress in a user is disclosed. The method includes mixing reduced glutathione powder and deoxygenated water in an anaerobic environment to form a reduced glutathione solution. The method includes packaging the reduced glutathione solution in an airless dispenser in an anaerobic environment such that the reduced glutathione is not substantially exposed to an oxygen source from manufacture to dispensing.

In an embodiment of the disclosure, reduced glutathione is dissolved in a deoxygenated water solvent. The deoxygenated water solvent has had dissolved oxygen ($O_2$) gasses removed from the water. Various techniques for removing dissolved oxygen from water are known in the art, including for example, boiling water at atmospheric pressure, boiling water at reduced pressure, purging water with nitrogen gas ($N_2$), argon gas (Ar), or other inert gas, and sonication of the water under reduced pressure. Additionally, water deoxygenation may be performed by bio reactive processes including, for example, yeast-based bio reactive processes. In an embodiment, highly pure deoxygenated water is utilized in combination with other components of the composition disclosed herein.

In an embodiment, the composition is encapsulated in a liposome structure. The liposome structure may be a spherical lipid-based vesicle constructed from sunflower-based lecithin rich in plant-based phospholipids. The liposome structure may have a hollow core including an aqueous solution of the reduced glutathione in deoxygenated water with other components as disclosed herein. The liposome structure may provide enhanced and targeted delivery to a user through the user's oral, esophageal, and gastrointestinal mucosa lining. It should be appreciated that the liposome structure may comprise any suitable liposome structure and is not limited to a spherical lipid-based vesicle from sunflower-based lecithin. Sunflower-based lecithin has a low affinity for allergenic response as compared to soy lecithin and may be advantageous for certain users who are disposed to allergenic reactions.

The liposome structure of the disclosure comprises a natural positive charge and has a high affinity for mucosal binding. In an embodiment, the liposome structure is configured to provide gradual delivery of the deoxygenated aqueous reduced glutathione solution from the liposome core through the mucosal lining of a user into the user's bloodstream.

In an embodiment, the phospholipids in the lecithin are responsible for organized formation of a liposome vesicle by providing lipid molecules, especially phosphatidylcholine, containing a hydrophilic head and hydrophobic tail, that has a binding capacity to form a spherical vesicle including at least one lipid bilayer. The hydrophilic head is located on an outer shell and the hydrophobic tail is oriented toward an inner surface of the vesicle shell. A liposome has an aqueous solution core surrounded by a hydrophobic membrane in the form of a lipid bilayer. Hydrophilic solutes, such as reduced glutathione, are dissolved in the core and cannot readily pass through the lipid bilayer. To deliver the molecules to a site of action, the lipid bilayer may fuse with other bilayers, such as a cell wall, and deliver the liposome contents.

In an embodiment, the liposome structure is defined as a distribution of Small Unilayer Vesicles (SUV) and Large Unilayer Vesicles (LUV). SUV liposomes are defined as a single unilayer vesicle having a diameter between about 20 nm to about 100 nm. LUV liposomes are defined as a single inlayer vesicle having a diameter between about 100 nm to about 400 nm. In an embodiment, the majority of the liposomes in the formulation are of the SUV type. In an embodiment, the composition includes a higher loading of lecithin to provide more phospholipids to maximize the number of liposomes in the composition. In an embodiment, the liposomes comprise more than 8 wt % the total composition. In an embodiment, the liposomes comprise more than 10 wt % the total composition. An increased liposomal population may maximize the encapsulation of the deoxygenated aqueous reduced glutathione and solute to a theoretical efficiency of about 50% of the aqueous medium.

In an embodiment, liposomes of the composition primarily perform the function of targeted delivery and slow release of the deoxygenated aqueous reduced glutathione. Further, some oxidative protection is afforded by the liposome vesicle in the form of an oxygen permeability rate limited reducing oxidation of the internal contents after dispensing the composition. During storage in the consumer liquid product package, which in an embodiment includes an airless dispenser, eventually all components of the composition will reach a similar oxygen saturation and level.

Referring now to the figures, FIG. 1 illustrates the chemical structure 100 of reduced glutathione. As illustrated, reduced glutathione comprises glutamic acid 102, cysteine 104, and glycine 106. Reduced glutathione (GSH) is a linear tripetide of L-glutamine, L-cysteine, and glycine. Reduced glutathione is technically referred to as N-L-gamma-glutamyl-cysteinyl glycine or L-glutathione. The molecule includes a sulfhydryl (SH) group on the cysteinyl portion that accounts for its strong electron-donating character that enables glutathione to be effective in reducing oxidative stress in the body. Glutathione is oxidized as an electron is lost, and two such molecules (with a lost electron) become linked or dimerized by a disulfide bridge. The dimerized molecules form glutathione disulfide or oxidized glutathione (GSSG). The linkage is reversible upon re-reduction.

The synthesis of reduced glutathione includes two closely linked and enzymatically-controlled reactions that utilize adenosine triphosphate (ATP). First, cysteine and glutamate are combined by gamma-glutamyl cysteinyl synthetase. Second, reduced glutathione synthetase combines gamma-glutamylcysteine with glycine to generate reduced glutathione. As the levels of reduced glutathione rise, the processes are self-limited against further production of reduced glutathione. Otherwise, cysteine availability is usually rate-limiting. Fasting, protein-energy malnutrition, and other dietary amino acid deficiencies limit the synthesis of reduced glutathione. The recycling of reduced glutathione is catalyzed by glutathione disulfide reductase, which uses reducing equivalents from nicotinamide adenine dinucleotide phosphate (NADPH) to reconvert oxidized glutathione to glutathione disulfide. The reducing power of ascorbate helps conserve systemic reduced glutathione.

Figure 2:
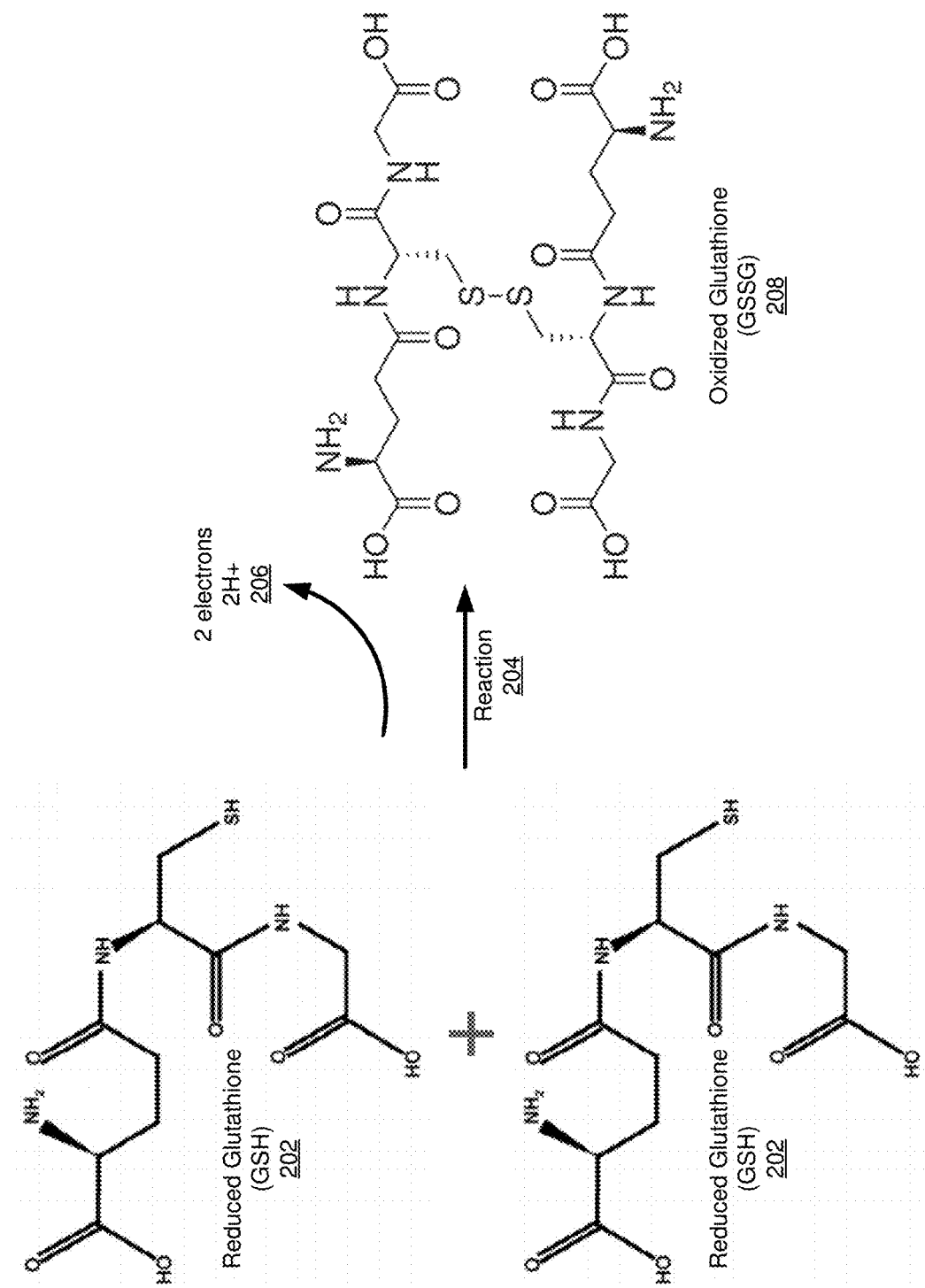
FIG. 2 illustrates the chemical oxidation reaction of reduced glutathione (GSH) to oxidized glutathione (GSSG) according to one implementation consistent with the teachings and principles of the disclosure.

FIG. 2 illustrates the oxidation reaction 204 of reduced glutathione (GSH) 202 to oxidized glutathione (GSSG) 208. The reaction 204 produces two electrons and two protons as illustrated at 206.

In an embodiment of the disclosure, a composition is provided to a user. The composition includes 99.9% purity reduced glutathione powder. The reduced glutathione powder is solubilized in a deoxygenated water solvent and encapsulated in a plant-based phospholipid liposome structure. The composition includes an effective amount of *stevia*, natural lemon essential oil, and natural peppermint essential for improving the overall flavor of the composition for human oral consumption. In an embodiment, the composition includes from about 525 mg to about 575 mg of reduced glutathione per 4 g of solution.

In an embodiment, the resulting liquid composition is packaged in an airless dispenser that is configured to maintain the composition in an anaerobic environment. As such, the airless dispenser protects the reduced glutathione from degradation and conversion to oxidized glutathione. Applicant recognizes that previous purported supplements including reduced glutathione suffer from a sulfur smell due to the strong oxidation of reduced glutathione. As such, the airless dispenser extends the effective shelf-life of the reduced glutathione in the present disclosure by substantially eliminating contact of the reduced glutathione with oxygen, even after first use of the composition. Applicant recognizes that other forms of packaging and delivery result in the reduced glutathione making contact with oxygen and thus rapidly degrading and oxidizing into oxidized glutathione, even if a successful manufacture of reduced glutathione is initially achieved.

Clinical Example

In one study conducted to test the effectiveness of a composition comprising reduced glutathione as disclosed above, the bio-effectiveness and availability of reduced glutathione in the body was greatly enhanced compared with purported GSH supplements known in the art. The composition provided unexpectedly good results given that purported GSH supplements known in the art in fact fail to deliver reduced glutathione to the user.

In one clinical study, a composition including reduced glutathione in a deoxygenated water solvent was provided to a user. The composition was encapsulated in a phospholipid liposome structure and packaged and delivered from an airless dispenser. The composition included 550±2 mg of reduced glutathione per 4 g of solution. The composition was provided to three human volunteers as a liquid-based oral supplement, and it was provided to one human volunteer as a liquid-based topical treatment to be applied topically. The human serum levels of reduced glutathione and oxidized glutathione were sampled initially before ingestion to establish a baseline level, and the serum levels were again sampled three times over eight hours after ingestion or application of the composition. The participants continued to take the composition once every morning at least thirty minutes before meals for four weeks. The serum levels of the participants were sampled once each week during the four-week study period to collect data for long-term effects of the composition.

Each participant experienced a short-term increase in serum levels of reduced glutathione equal to at least a 30% increase in the presence of reduced glutathione in the serum. Each participant experienced a long-term progressive reduction of oxidized glutathione equal to at least a 30% reduction in the presence of oxidized glutathione in the serum. As discussed previously, the ratio of reduced glutathione to oxidized glutathione is an important and well-understood marker for cellular oxidative stress. The results of the clinical example indicate that the composition was bioavailable unlike other pill and capsule delivery forms of purported GSH supplements. Further, the composition provided long-term reduction in systemic cellular oxidative stress in each of the participants.

In the above-referenced study, four persons agreed to participate. The participants included one male and one female ranging in age from 23 to 83 years of age. The participants were assigned a number from #1 to #4 as follows: (1) 61-year-old female, (2) 55-year-old male, (3) 23-year-old female, and (4) 83-year-old female. Each of the participants was permitted to each the morning of the first serum collection but refrained from taking antioxidant dietary supplements during the course of the four-week study period. The participants' blood was collected for baseline measurements at approximately 8:00 AM by intravenous puncture. The serum was extracted, processed, and frozen for later analysis. After the collection of the baseline serum sample, the participants immediately consumed the composition by dispensing 4 mL of the liquid composition into their mouth and swishing for 15-20 seconds before swallowing. The participants refrained from drinking for 15 minutes afterward. The participant who used the product topically applied approximately the same amount of the composition onto the abdomen and soft areas under the arms. Samples of the participants' blood were against collected at 2 hours, 6 hours, and 8 hours after the first collection. The participants consumed the composition one time per day in the morning for a four-week period. The participants' blood was collected each week at exactly seven-day intervals for four weeks at approximately 10:00 AM. The participants were instructed to consume the composition four hours prior to collection. The serum was extracted, processed, and frozen for later analysis. All serum samples were assayed within thirty days of collection.

Analysis of the Serum Samples.

The serum samples were analyzed to determine the levels of reduced glutathione and oxidized glutathione. The serum samples were analyzed using the BioVision (Milpitas, Calif.) Glutathione Fluorometric Assay Kit (GSH, GSSG, and Total) k264. Wasatch Scientific Laboratories in Murray, Utah, USA was contracted to perform the assay using the BioVision fluorometric kit and method. Whole blood samples were collected and immediately centrifuged to separate the serum from the red blood cells and heavier components. Approximately 120 μL of serum was added to 40 μL of an ice-cold perchloric acid PCA buffer in a 1 mL aliquot. The solution was vortexed and stored on ice for five minutes. The solution was centrifuged at 13,000 G for two minutes, and the supernatant was collected and frozen at −60 degC.

Figure 3:
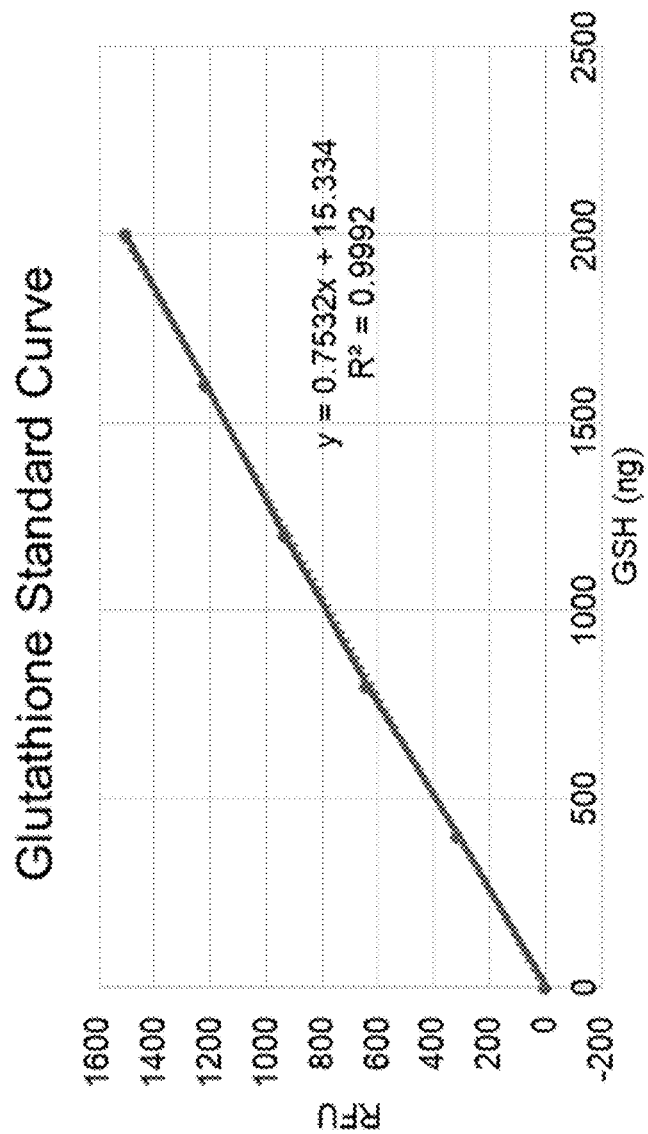
FIG. 3 illustrates a standard curve for reduced glutathione resulting from a short-term analysis of a clinical example consistent with the teachings and principles of the disclosure.

FIG. 3 illustrates a standard curve for reduced glutathione for the short-term analysis. The standard curve for reduced glutathione and oxidized glutathione were created, and then the prepared serum samples were tested at two dilutions to determine the optimal dilution for the best dynamic resolution of the assay. The samples were processed and assayed in duplicate pairs at the chosen dilution. The results of each pair were reviewed and compared for repeatability and best-fit samples were used. FIG. 3 illustrates a mass of reduced glutathione (GSH) in nanograms on the x-axis plotted against the relative fluorescence units (RFU) on the y-axis.

Figure 4:
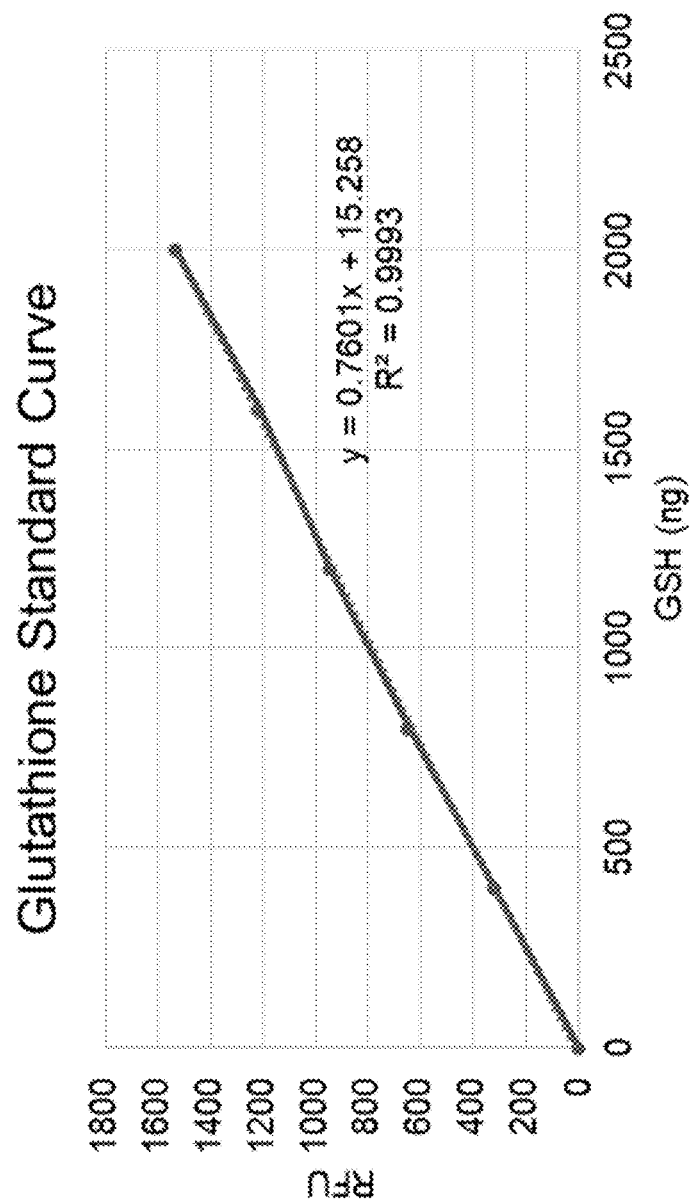
FIG. 4 illustrates a standard curve for reduced glutathione resulting from a long-term analysis of a clinical example consistent with the teachings and principles of the disclosure.

FIG. 4 illustrates a standard curve for reduced glutathione for the long-term analysis. The standard curve for reduced glutathione and oxidized glutathione were created, and then the prepared serum samples were tested at two dilutions to determine the optimal dilution for the best dynamic resolution of the assay. The samples were processed and assayed in duplicate pairs at the chosen dilution. The results of each pair were reviewed and compared for repeatability and best-fit samples were used. FIG. 3 illustrates a mass of reduced glutathione (GSH) in nanograms on the x-axis plotted against the relative fluorescence units (RFU) on the y-axis. The results of the assay were compiled and displayed in tabular and graphical form. In addition, ratiometric results of reduced glutathione (GSH) and oxidized glutathione (GSSG) were created for each sample.

Figure 5:
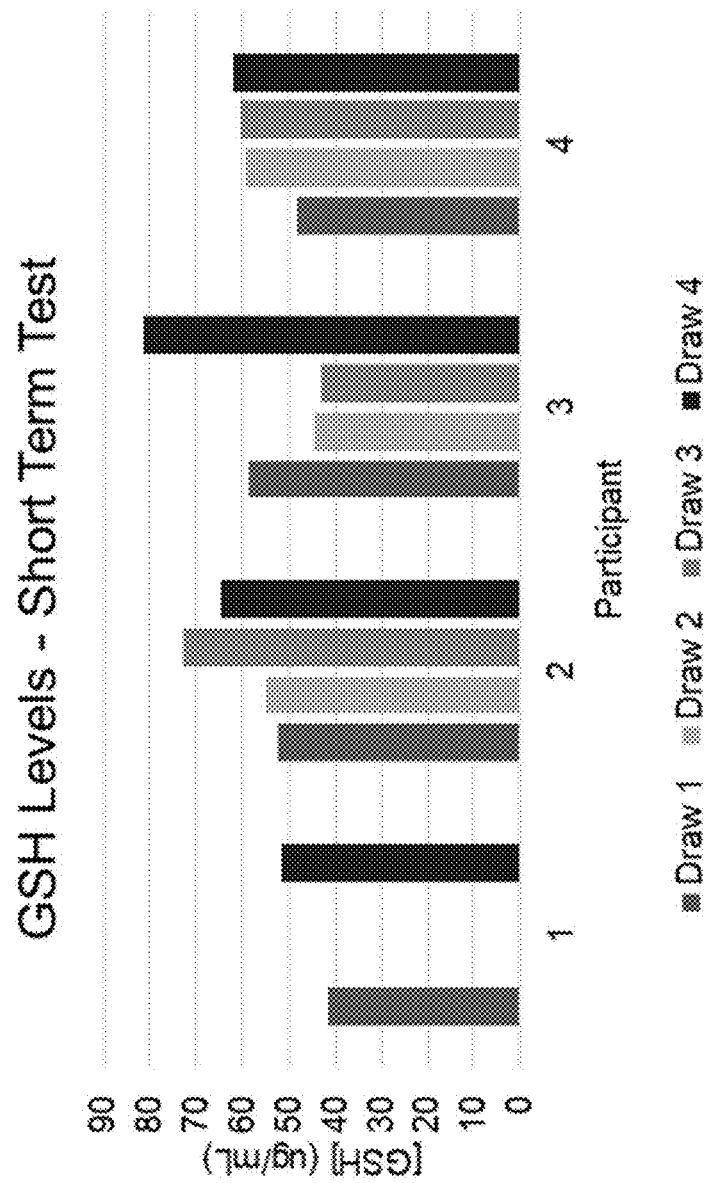
FIG. 5 illustrates concentrations of reduced glutathione resulting from a short-term analysis of a clinical example consistent with the teachings and principles of the disclosure.

FIG. 5 illustrates concentrations of reduced glutathione for each of the four aforementioned participants for the short-term analysis. FIG. 5 illustrates concentrations in μg/mL for each of four possible serum draws for each of the four participants. Draw one is the baseline draw. Draw two was taken at the baseline plus four hours. Draw three was taken at the baseline plus six hours. Draw four was taken at the baseline plus eight hours. As illustrated in FIG. 5, all participants in the short-term analysis experienced an increase in serum levels of reduced glutathione. The increase concentration of reduced glutathione appeared to peak at approximately six to eight hours after ingestion. The increase in reduced glutathione was on average 30% above baseline levels. Participant one, a female, applied the composition topically and experienced elevated serum levels of reduced glutathione.

Figure 6:
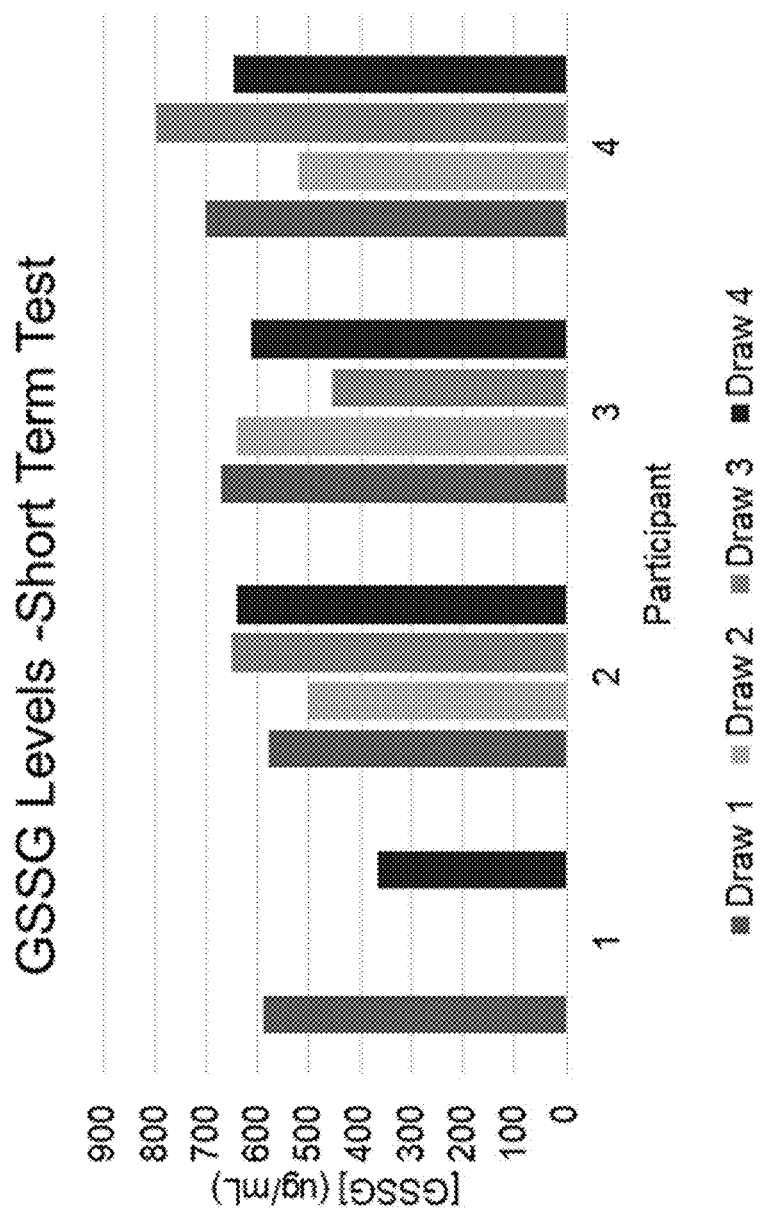
FIG. 6 illustrates concentrations of oxidized glutathione resulting from a short-term analysis of a clinical example consistent with the teachings and principles of the disclosure.

FIG. 6 illustrates concentrations of oxidized glutathione for each of the four aforementioned participants for the short-term analysis. FIG. 6 illustrates concentrations in μg/mL for each of four possible serum draws for each of the four participants. Draw one is the baseline draw. Draw two was taken at the baseline plus four hours. Draw three was taken at the baseline plus six hours. Draw four was taken at the baseline plus eight hours. Participant one, a female, applied the composition topically and experienced elevated serum levels of reduced glutathione. As illustrated in FIG. 6, concentrations of oxidized glutathione appeared to respond differently for each participant. The most significant change in levels of oxidized glutathione was an almost 50% reduction in participant one who applied the composition topically. In participants three and four, the levels of oxidized glutathione on average reduced slightly from baseline.

Figure 7:
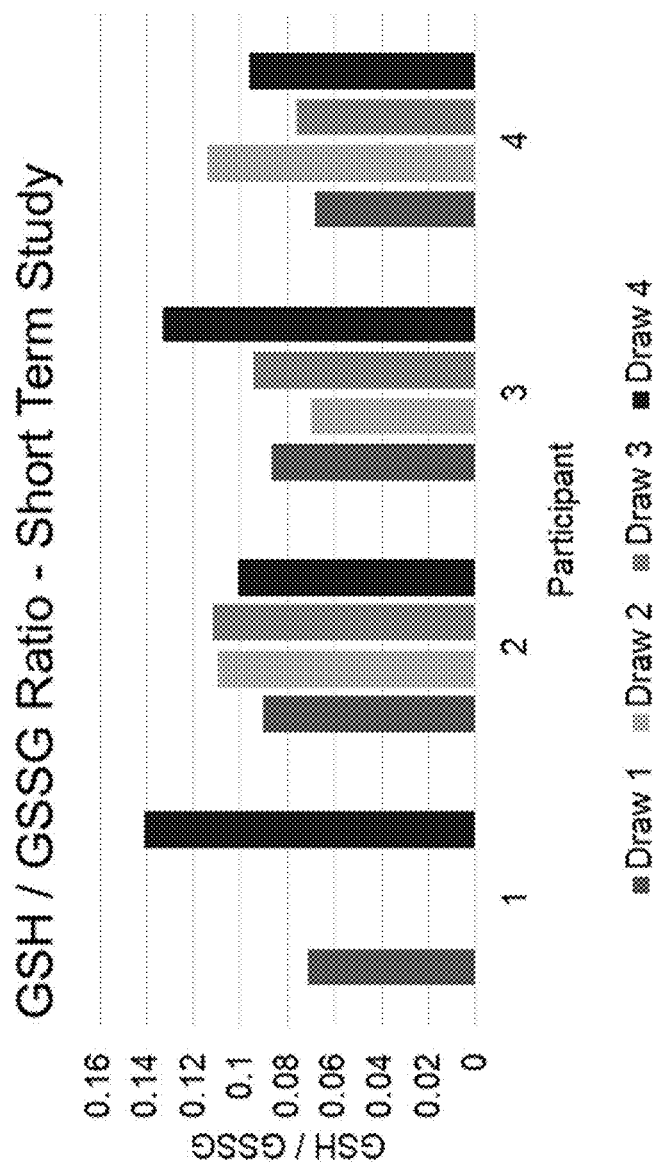
FIG. 7 illustrates ratios of reduced glutathione to oxidized glutathione resulting from a short-term analysis of a clinical example consistent with the teachings and principles of the disclosure.

FIG. 7 illustrates the ratios of reduced glutathione to oxidized glutathione for each of the participants for the short-term analysis. As illustrated in FIG. 7, the composition provided a short-term antioxidant benefit to each of the participants. The reduced/oxidized glutathione ratio is an accepted standard to measure cellular oxidative stress. This study illustrates the redox ratio trend over time. After ingestion, each participant experienced an increase in the redox ratio compared to the baseline, even eight hours after consuming or applying the composition. This study demonstrates bio-utilization of the redox ratio.

Figure 8:
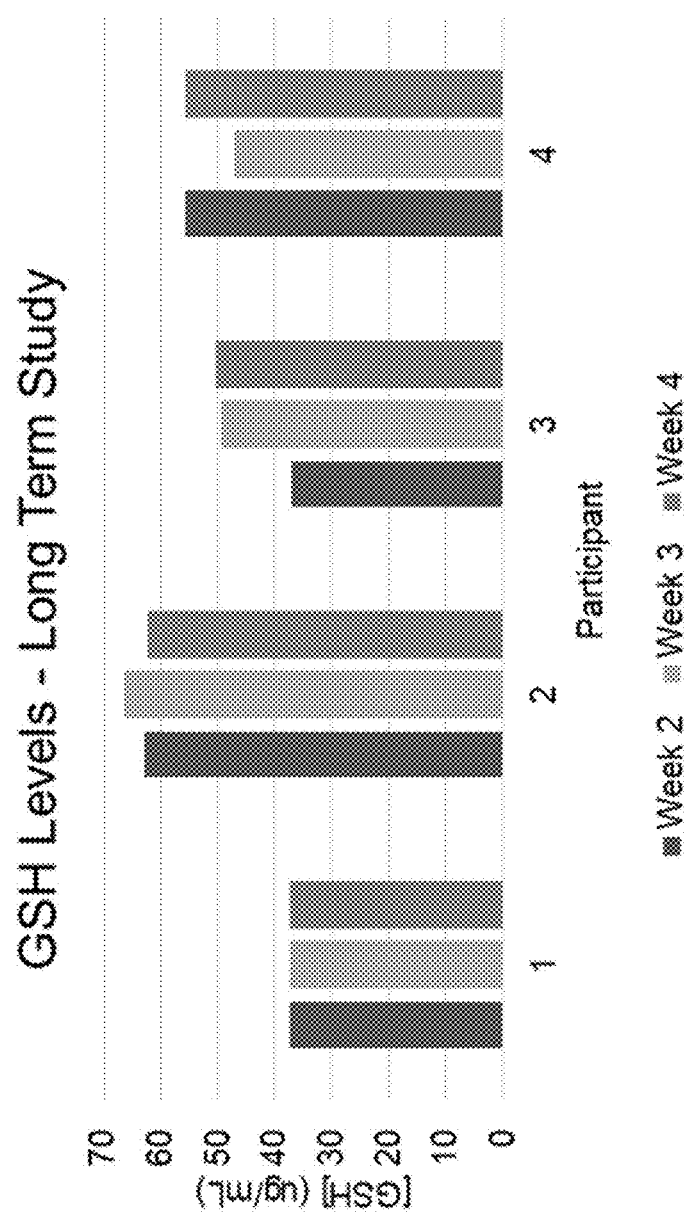
FIG. 8 illustrates concentrations of reduced glutathione resulting from a long-term analysis of a clinical example consistent with the teachings and principles of the disclosure.

FIG. 8 illustrates concentrations of reduced glutathione for each of the four aforementioned participants for the long-term analysis. FIG. 8 illustrates concentrations in μg/mL for each of three weekly serum draws for each of the four participants. Draw one (not shown due to laboratory error) was taken at 10:00 AM exactly one week after ingestion or application of the composition. Draw two occurred at 10:00 AM two weeks after ingestion or application of the composition. Draw three occurred at 10:00 AM exactly three weeks after ingestion or application of the composition. Draw four occurred at 10:00 AM exactly four weeks after ingestion or application of the composition. The human serum samples were assayed for concentrations of reduced and oxidized glutathione. Participant one, a female, applied the composition topically and participants two, three, and four ingested orally a liquid-based composition.

As illustrated in FIG. 8, the participants' serum levels of reduced glutathione show mixed results. Participants one and three demonstrates levels of reduced glutathione that are very close to the baseline levels without significant increase. Participants two and four demonstrated long-term increase in levels of reduced glutathione equal to approximately 20-22%. The long-term serum levels of reduced glutathione when viewed alone showed positive results in participants two and four.

Figure 9:
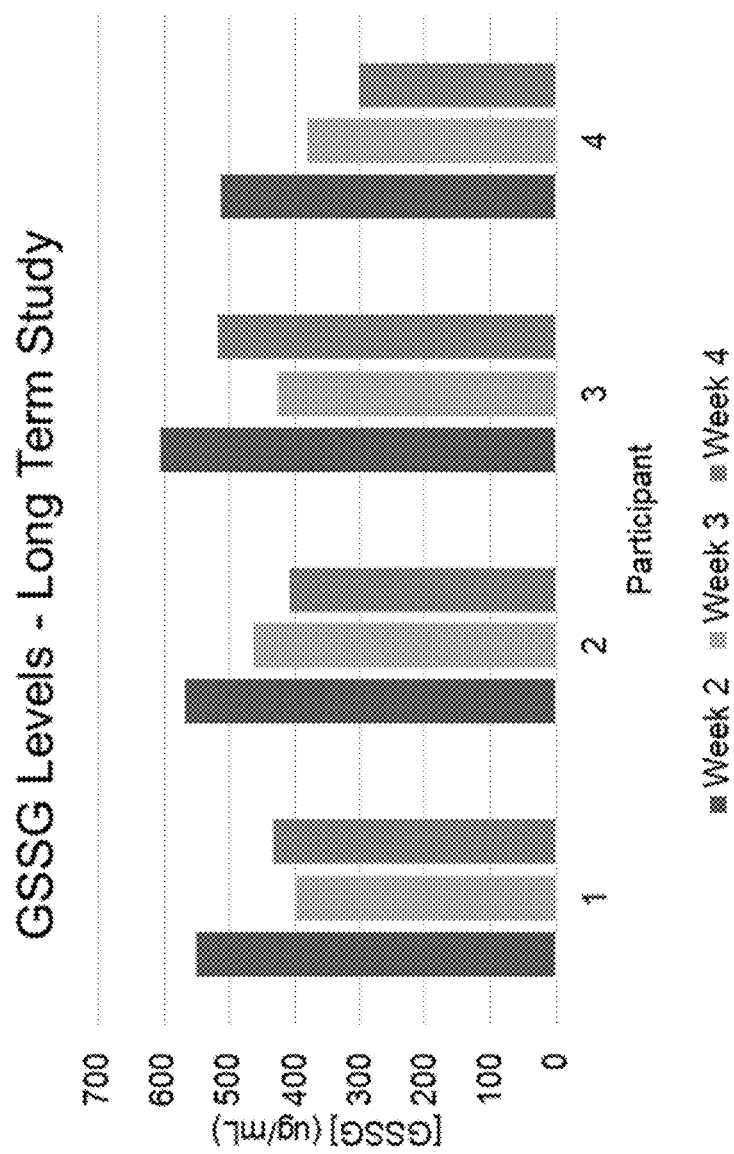
FIG. 9 illustrates concentrations of oxidized glutathione resulting from a long-term analysis of a clinical example consistent with the teachings and principles of the disclosure.

FIG. 9 illustrates concentrations of oxidized glutathione for each of the four aforementioned participants for the long-term analysis. FIG. 9 illustrates concentrations in μg/mL for each of three weekly serum draws for each of the four participants. Draw one (not shown due to laboratory error) was taken at 10:00 AM exactly one week after ingestion or application of the composition. Draw two occurred at 10:00 AM two weeks after ingestion or application of the composition. Draw three occurred at 10:00 AM exactly three weeks after ingestion or application of the composition. Draw four occurred at 10:00 AM exactly four weeks after ingestion or application of the composition. The human serum samples were assayed for concentrations of reduced and oxidized glutathione. Participant one, a female, applied the composition topically and participants two, three, and four ingested orally a liquid-based composition.

As illustrated in FIG. 9, each of the four participants experienced a significant decrease in long-term concentrations of oxidized glutathione (GSSG). As discussed previously, reduced glutathione is oxidized inside cells and converted to oxidized glutathione according to the reaction 200 illustrated in FIG. 2. A portion of the oxidized glutathione is shuttled out of the cells and into the intracellular space and into the blood. When the ratio of reduced/oxidized glutathione is calculated, a true reduction is cellular oxidation is evidence.

Figure 10:
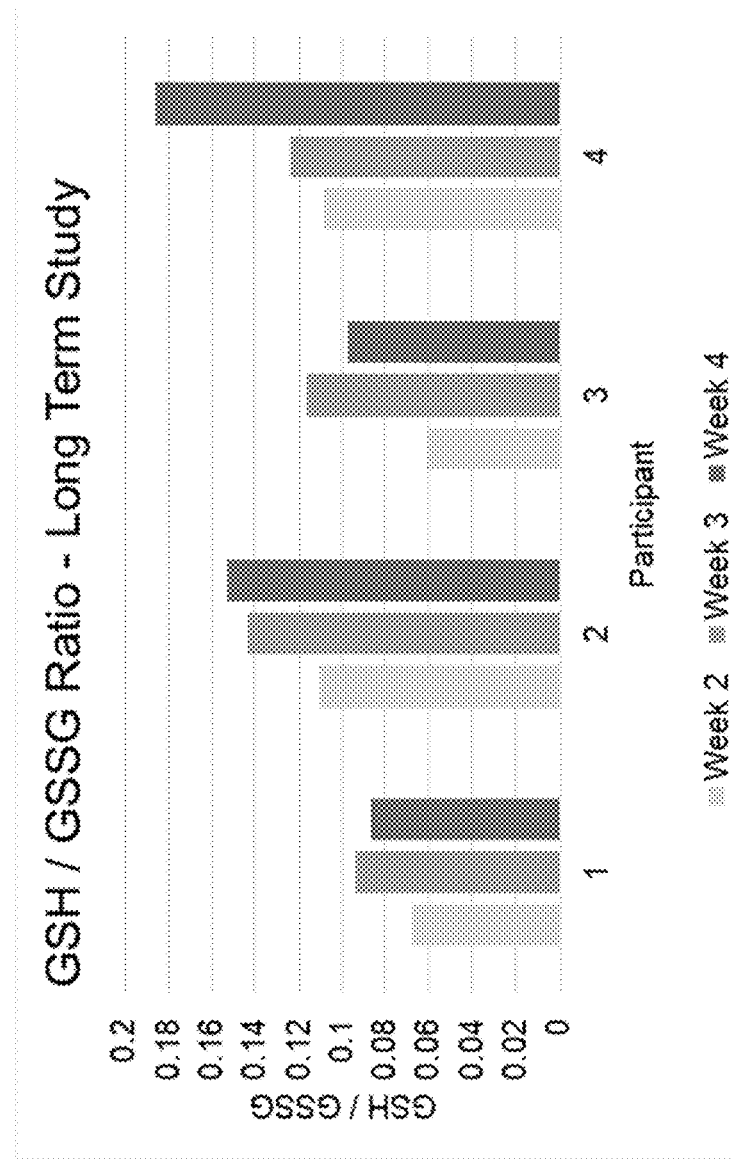
FIG. 10 illustrates ratios of reduced glutathione to oxidized glutathione resulting from a long-term analysis of a clinical example consistent with the teachings and principles of the disclosure.

FIG. 10 illustrates the ratios of reduced glutathione to oxidized glutathione for each of the four aforementioned participants for the long-term analysis. As illustrated in FIG. 10, each of the participants experienced a sustained and cumulative decrease in oxidative stress. The reduced/oxidized glutathione redox ratio increased for all participants over the four weeks of ingesting or applying the composition. Applicant notes that participant three and participant four represent a wide age and health gap, where one is a 23-year-old healthy female and the other is an 83-year old female with health issues due to age. The composition had a positive long-term effect in both the young participant and the older participant, where the older participant experienced a greater rise in the redox ratio. The data further shows that participant one experienced a redox benefit, even by applying the product topically. Applicant notes that participant one only applied about one-third of the dose compared to the oral participants, not following specific dosing instructions. The results for all participants clearly demonstrates the benefits of the novel composition comprising reduced glutathione that is disclosed herein.

Figure 11:
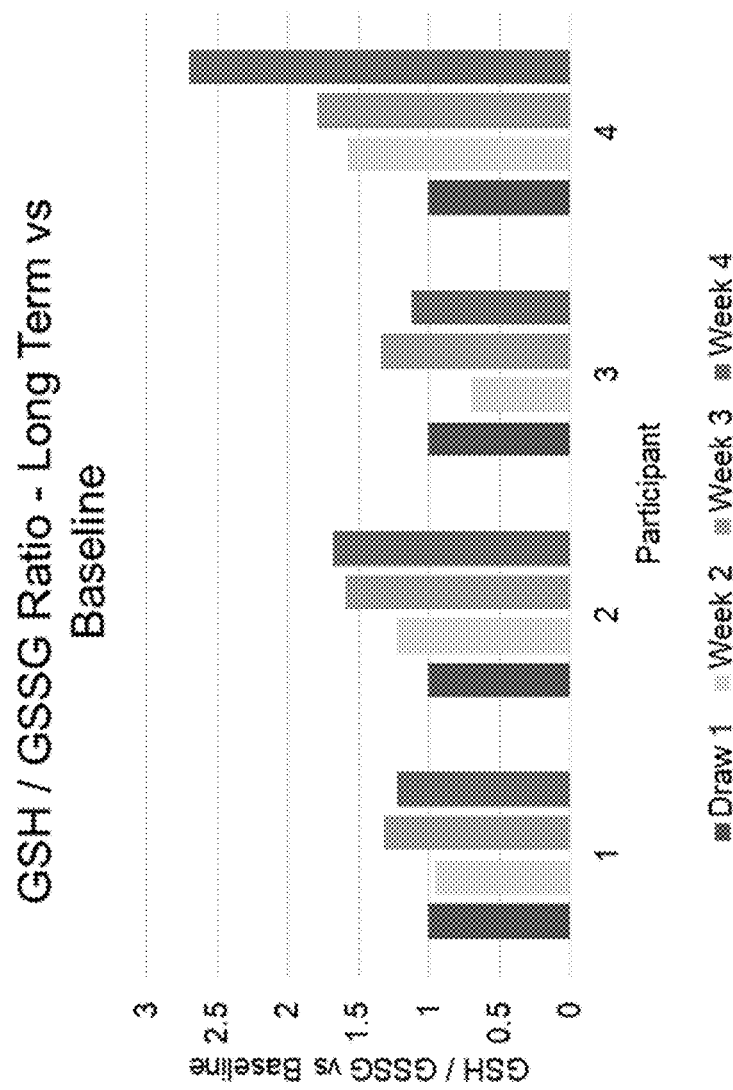
FIG. 11 illustrates ratios of reduced glutathione to oxidized glutathione resulting from a long-term analysis versus the baseline analysis of a clinical example consistent with the teachings and principles of the disclosure.

FIG. 11 illustrates the ratios of reduced glutathione to oxidized glutathione for each of the participants for the long-term analysis versus the baseline analysis. FIG. 11 illustrates a comparison of the change in redox over time as a result of supplementation with the composition disclosed herein. As illustrated in FIG. 11, all participants experienced a net average increase above baseline redox ratios, with participant two (55-year-old male) and participant four (83-year-old female) experiencing the greatest increase. Applicant notes that it is anticipated that participant one (61-year-old female) would have experienced a greater result if the dosage requirements for topical application were followed more consistently.

The effects of the novel composition comprising reduced glutathione that is disclosed herein indicate a bioavailability of reduced glutathione and its short-term and long-term benefits in the human body as indicated in the serum concentrations of reduced glutathione (GSH) and oxidized glutathione (GSSG). All participants experienced a noticeable increase in GSH/GSSG redox ratio indicating a true reduction in cellular oxidative stress, with the older participants (age 55-83) experiencing higher ratios. This is consistent with the assumption that older participants have a greater amount of cellular oxidative stress to be reduced.

The results of the clinical example demonstrate conclusively that the composition disclosed herein is effectively delivering reduced glutathione. The composition includes reduced glutathione and a deoxygenated water solvent. The composition is manufactured and packaged in an anaerobic environment, in stark contrast with previous supplements known in the art that purport to deliver reduced glutathione but instead deliver oxidized glutathione. The careful maintenance of an anaerobic condition, as disclosed herein, provides the unexpected result (given all prior failures) of a composition that genuinely comprises reduced glutathione. The composition disclosed herein provides increased levels of reduced glutathione, reduced cellular oxidative stress, and provides all the appurtenant benefits.

It should be appreciated that in various embodiments, dosage amounts may be adjusted depending on the effect on any given individual, as well as the biometrics of that individual. For example, a larger person may require a higher dosage than a smaller person. Similarly, a person suffering from an acute condition may benefit from a higher dose for a time until the condition is controlled, at which point a lower dose may provide sufficient management over time.

Referring now to FIG. 12, a schematic block diagram of a method 1200 for reducing oxidative stress in a user is illustrated. The method 1200 begins and a composition is provided to a user at 1202. The composition comprises an effective amount of reduced glutathione for reducing oxidative stress in the user and a deoxygenated water solvent.

FIG. 13 illustrates a schematic block diagram of a method 1300 for reducing oxidative stress in a user. The method 1300 beings and a composition is provided to a user at 1302. The composition includes an effective amount of reduced glutathione for reducing oxidative stress in the user, a deoxygenated water solvent, an effect amount of one or more preservatives, and an effective amount of one or more natural flavoring components for improving an overall flavor of the composition. The composition is such that the reduced glutathione comprises from about 8% to about 14% by weight of the total composition. The composition is such that the reduced glutathione comprises a purity from about 98% to about 99.9% purity. The composition is encapsulated in a phospholipid liposome structure. The composition is packaged in an airless dispenser configured to maintain an anaerobic environment.

In one embodiment, the composition may be provided for the treatment of cellular oxidative stress. When the composition is provided for the treatment of cellular oxidative stress, it may be ingested orally or administered topically. Applicant notes that in further embodiments the composition may be administered intravenously or intramuscularly, or in a tablet or powder form without departing from the scope of the disclosure.

In one embodiment, the composition is provided for the treatment of acute levels of free radicals in the body. In such an embodiment, the composition may be prepared for immediate intravenous or intramuscular administration. The composition may further or alternatively be provided for oral ingestion or topical application. In such an embodiment, the composition may be provided for regular administration after acute levels of free radicals in the body have been treated and reduced to safe levels.

In one embodiment, the composition is provided for the treatment of acetaminophen overdose. The molecule known as N-acetylcysteine (hereinafter "NAC") is known in the art for the treatment of acetaminophen overdose. Pharmaceutical NAC is primarily used in medical settings for respiratory conditions, to manage acetaminophen overdose, and to prevent radio-contrast-induced nephropathy. However, the half-life of NAC is approximately 5.6 hours, and 30% of NAC is renally excreted by the body. Orally administered or inhaled NAC is associated with drowsiness, stomatitis, clamminess, rhinorrhea, and hemoptysis, and NAC is a category B pregnancy risk. In contrast with NAC, where the half-life is extremely short and the molecule is unstable, the shelf-life of the composition disclosed herein is at least one year. Therefore, the composition disclosed herein provides an alternative to NAC that is shelf-stable for an extended period and demonstrates high viability and efficacy.

In one embodiment, a 99.9% purity reduced glutathione powder is solubilized in deoxygenated water and encapsulated in a plant-based phospholipid liposome structure. In the embodiment, the composition includes from about 8% to about 14% by weight reduced glutathione. The composition includes from about 4% to about 11% by weight sunflower lecithin. The composition includes from about 0.2% to about 0.6% by weight lemon essential oil. The composition includes from about 0.1% to about 0.5% peppermint essential oil. The composition includes from about 0.01% to about 0.25% stevia extract. The composition includes sodium benzoate and potassium sorbate.

In an embodiment of the disclosure, the composition includes highly pure L-glutathione reduced. In an embodiment of the disclosure, the reduced glutathione comprises a purity from about 98% to about 99.9% purity. In an embodiment, the purity is from about 90% to about 99.9% purity. In an embodiment, the purity is from about 95% to about 99.9% purity. In an embodiment, the purity is from about 99.0% to about 99.9% purity. It should be appreciated that various ranges of purity may be extracted from any of the aforementioned ranges as if those ranges were disclosed explicitly.

In an embodiment of the disclosure, the composition includes sunflower lecithin. Lecithin is a fat found in a plurality of food products. Sunflower lecithin is a phospholipid comprising phosphatidylcholine, phosphatidylinositol, phosphatidylethanolamine, and omega-6 linoleic acid. Sunflower lecithin is associated with processing fats and supporting cell membranes. In an embodiment of the disclosure, the sunflower lecithin is provided for encapsulating the composition and protecting the reduced glutathione component.

In an embodiment of the disclosure, the composition includes lemon essential oil. Lemon essential oil may be provided to improve an overall flavor of the composition. As disclosed, oxidized glutathione provides a sulfur smell that may be pungent or off-putting to a user. Additionally, the composition of the present disclosure may oxidize with oxygen in the air when the composition is being ingested, and the oxidized may cause the composition to become unpalatable to the user immediately before the user ingests the composition. The lemon essential oil may be provided to counteract the sulfur smell of the oxidized glutathione and increase the flavor of the composition.

In an embodiment of the disclosure, the composition includes peppermint essential oil. As discussed previously with respect to the lemon essential oil, the peppermint essential oil may be provided to improve the overall flavor of the composition and mask a sulfur smell arising from the oxidation of the reduced glutathione.

In an embodiment of the disclosure, the composition includes stevia extract. As discussed previously with respect to the lemon essential oil and/or the peppermint essential oil, the stevia extract may be provided to improve the overall flavor of the composition and mask a sulfur smell arising from the oxidation of the reduced glutathione.

In an embodiment of the disclosure, the composition includes sodium benzoate. Sodium has a chemical formula of $NaC_7H_5O_2$. Sodium benzoate is known as a food preservative and has an E number of E211. Sodium benzoate is the sodium salt of benzoic acid and exists in the form when dissolved in water. As a food additive, sodium benzoate is bacteriostatic and fungistatic under acidic condition. Sodium benzoate is included in the composition as a preservative in an embodiment of the disclosure.

In an embodiment of the disclosure, the composition includes potassium sorbate. Potassium sorbate has a chemical formula of $CH_3CH=CH-CH=CH-CO_2K$. Potassium sorbate is a known food preservative and has an E number of E202. Potassium sorbate is known for inhibiting molds and yeasts in a variety of foods and liquids. Potassium sorbate is included in the composition as a preservative in an embodiment of the disclosure.

EXAMPLES

Chart 1 below shows an example embodiment of the composition. Components were dissolved in deoxygenated water and encapsulated in a plant-based phospholipid liposome structure. The composition was packaged and stored in an airless dispenser.

CHART 1

| Component | Weight Percent Total Composition |
|---|---|
| L-glutathione reduced | 14.00 |
| Sunflower lecithin | 10.50 |
| Lemon essential oil | 0.40 |
| Peppermint essential oil | 0.25 |
| Sodium benzoate | 0.10 |
| Potassium sorbate | 0.10 |
| Stevia extract | 0.10 |

Chart 2 below shows an example embodiment of the composition. Components were dissolved in deoxygenated water and encapsulated in a plant-based phospholipid liposome structure. The composition was packaged and stored in an airless dispenser.

CHART 2

| Component | Weight Percent Total Composition |
|---|---|
| L-glutathione reduced | 10.00 |
| Sunflower lecithin | 10.50 |
| Lemon essential oil | 0.40 |
| Peppermint essential oil | 0.25 |
| Sodium benzoate | 0.10 |
| Potassium sorbate | 0.10 |
| Stevia extract | 0.10 |

Chart 3 below shows an example embodiment of the composition. Components were dissolved in deoxygenated water and encapsulated in a plant-based phospholipid liposome structure. The composition was packaged and stored in an airless dispenser.

CHART 3

| Component | Weight Percent Total Composition |
|---|---|
| L-glutathione reduced | 8.00 |
| Sunflower lecithin | 10.50 |
| Lemon essential oil | 0.40 |
| Peppermint essential oil | 0.25 |
| Sodium benzoate | 0.10 |
| Potassium sorbate | 0.10 |
| Stevia extract | 0.10 |

Chart 4 below shows an example embodiment of the composition. Components were dissolved in deoxygenated water and encapsulated in a plant-based phospholipid liposome structure. The composition was packaged and stored in an airless dispenser.

CHART 4

| Component | Weight Percent Total Composition |
|---|---|
| L-glutathione reduced | 14.00 |
| Sunflower lecithin | 4.00 |
| Lemon essential oil | 0.40 |
| Peppermint essential oil | 0.25 |
| Sodium benzoate | 0.10 |
| Potassium sorbate | 0.10 |
| Stevia extract | 0.10 |

Chart 5 below shows an example embodiment of the composition. Components were dissolved in deoxygenated water and encapsulated in a plant-based phospholipid liposome structure. The composition was packaged and stored in an airless dispenser.

CHART 5

| Component | Weight Percent Total Composition |
|---|---|
| L-glutathione reduced | 14.00 |
| Sunflower lecithin | 11.00 |
| Lemon essential oil | 0.40 |
| Peppermint essential oil | 0.25 |
| Sodium benzoate | 0.10 |
| Potassium sorbate | 0.10 |
| Stevia extract | 0.10 |

Chart 6 below shows an example embodiment of the composition. Components were dissolved in deoxygenated water and encapsulated in a plant-based phospholipid liposome structure. The composition was packaged and stored in an airless dispenser.

CHART 6

| Component | Weight Percent Total Composition |
|---|---|
| L-glutathione reduced | 14.00 |
| Sunflower lecithin | 10.50 |
| Lemon essential oil | 0.20 |
| Peppermint essential oil | 0.25 |
| Sodium benzoate | 0.10 |
| Potassium sorbate | 0.10 |
| Stevia extract | 0.10 |

Chart 7 below shows an example embodiment of the composition. Components were dissolved in deoxygenated water and encapsulated in a plant-based phospholipid liposome structure. The composition was packaged and stored in an airless dispenser.

CHART 7

| Component | Weight Percent Total Composition |
|---|---|
| L-glutathione reduced | 14.00 |
| Sunflower lecithin | 10.50 |
| Lemon essential oil | 0.60 |
| Peppermint essential oil | 0.25 |
| Sodium benzoate | 0.10 |
| Potassium sorbate | 0.10 |
| Stevia extract | 0.10 |

Chart 8 below shows an example embodiment of the composition. Components were dissolved in deoxygenated water and encapsulated in a plant-based phospholipid liposome structure. The composition was packaged and stored in an airless dispenser.

CHART 8

| Component | Weight Percent Total Composition |
|---|---|
| L-glutathione reduced | 14.00 |
| Sunflower lecithin | 10.50 |
| Lemon essential oil | 0.40 |
| Peppermint essential oil | 0.10 |
| Sodium benzoate | 0.10 |
| Potassium sorbate | 0.10 |
| Stevia extract | 0.10 |

Chart 9 below shows an example embodiment of the composition. Components were dissolved in deoxygenated water and encapsulated in a plant-based phospholipid liposome structure. The composition was packaged and stored in an airless dispenser.

CHART 9

| Component | Weight Percent Total Composition |
|---|---|
| L-glutathione reduced | 14.00 |
| Sunflower lecithin | 10.50 |
| Lemon essential oil | 0.40 |
| Peppermint essential oil | 0.50 |
| Sodium benzoate | 0.10 |
| Potassium sorbate | 0.10 |
| Stevia extract | 0.10 |

Example 1 is a composition for reducing oxidative stress in a user. The composition includes an effective amount of reduced glutathione for reducing oxidative stress in the user, and deoxygenated water solvent.

Example 2 is a composition as in Example 1, wherein the composition is encapsulated in a phospholipid liposome structure.

Example 3 is a composition as in any of Examples 1-2, wherein the composition is packaged in an airless dispenser configured to maintain an anaerobic environment.

Example 4 is a composition as in any of Examples 1-3, wherein the reduced glutathione comprises from about 8% to about 14% by weight of the total composition.

Example 5 is a composition as in any of Examples 1-4, wherein the composition comprises from about 500 mg to about 600 mg reduced glutathione per 4 g of the composition.

Example 6 is a composition as in any of Examples 1-5, wherein the reduced glutathione comprises a purity from about 98% to about 99.9% purity.

Example 7 is a composition as in any of Examples 1-6, further comprising an effective amount of sodium benzoate for preserving the composition.

Example 8 is a composition as in any of Examples 1-7, further comprising an effective amount of potassium sorbate for preserving the composition.

Example 9 is a composition as in any of Examples 1-8, further comprising an effective amount of one or more natural flavoring components selected from a list comprising: lemon essential oil, peppermint essential oil, monk fruit extract, agave, honey, natural cane sugar, glucose, fruit concentrate, natural fruit powder, spearmint essential oil, wintergreen essential oil, orange essential oil, tangerine essential oil, lavender essential oil, and *stevia* extract.

Example 10 is a composition as in any of Examples 1-9, wherein the composition is prepared for liquid oral consumption.

Example 11 is a composition as in any of Examples 1-10, wherein the composition is prepared for topical application.

Example 12 is a composition as in any of Examples 1-11, wherein the composition is prepared for intravenous or intramuscular administration.

Example 13 is a composition as in any of Examples 1-12, wherein the reduced glutathione comprises from about 4 g to about 20 g per 100 mL of the deoxygenated water solvent.

Example 14 is a method of reducing oxidative stress in a user. The method includes providing a composition to the user, wherein the composition includes an effective amount of reduced glutathione for reducing oxidative stress in the user, and a deoxygenated water solvent.

Example 15 is a method as in Example 14, wherein the composition is encapsulated in a phospholipid liposome structure.

Example 16 is a method as in any of Example 14-15, wherein the composition is packaged in an airless dispenser configured to maintain an anaerobic environment.

Example 17 is a method as in any of Example 14-16, wherein the reduced glutathione comprises from about 8% to about 14% by weight of the total composition.

Example 18 is a method as in any of Example 14-17, wherein the composition comprises from about 500 mg to about 600 mg reduced glutathione per 4 g of the composition.

Example 19 is a method as in any of Example 14-18, wherein the reduced glutathione comprises a purity from about 98% to about 99.9% purity.

Example 20 is a method as in any of Example 14-19, wherein the reduced glutathione comprises a purity from about 99.0% to about 99.9% purity.

Example 21 is a method as in any of Example 14-20, wherein the composition further comprises an effective amount of sodium benzoate for preserving the composition.

Example 22 is a method as in any of Example 14-21, wherein the composition further comprises an effective amount of potassium sorbate for preserving the composition.

Example 23 is a method as in any of Example 14-22, wherein the composition further comprises an effective amount of one or more natural flavoring components selected from a list comprising: lemon essential oil, peppermint essential oil, monk fruit extract, agave, honey, natural cane sugar, glucose, fruit concentrate, natural fruit powder, spearmint essential oil, wintergreen essential oil, orange essential oil, tangerine essential oil, lavender essential oil, and *stevia* extract.

Example 24 is a method as in any of Example 14-23, wherein the composition is provided to the user for liquid oral consumption.

Example 25 is a method as in any of Example 14-24, wherein the composition is provided to the user for topical administration.

Example 26 is a method as in any of Example 14-25, wherein the composition is provided to the user for intravenous or intramuscular administration.

Example 27 is a method as in any of Example 14-26, wherein the reduced glutathione comprises from about 4 g to about 20 g per 100 mL of the deoxygenated water solvent.

Example 28 is a method as in any of Example 14-27, wherein the composition is provided to the user for short-term treatment of cellular oxidative stress.

Example 29 is a method as in any of Example 14-28, wherein the composition increases blood-serum levels of reduced glutathione in the user by at least 25%.

Example 30 is a method as in any of Example 14-29, wherein the composition is provided for long-term treatment of cellular oxidative stress.

According to one or more embodiments of the disclosure, a composition may include a combination of all or some, but not all, of the following ingredients:
  (a) L-glutathione reduced;
  (b) deoxygenated water;
  (c) sunflower lecithin;
  (d) lemon essential oil;
  % (e) peppermint essential oil;
  (f) sodium benzoate;
  (g) potassium sorbate; and/or
  (h) *stevia* extract.

Other embodiments of the composition may comprise, for example, concentrations of L-glutathione reduced as follows:
  (a1) from 5% to 20% by weight the total composition;
  (a2) from 6% to 19% by weight the total composition;
  (a3) from 7% to 18% by weight the total composition;
  (a4) from 8% to 17% by weight the total composition;
  (a5) from 8% to 16% by weight the total composition;
  (a6) from 8% to 15% by weight the total composition;
  (a7) from 8% to 14% by weight the total composition;
  (a8) from 8% to 13% by weight the total composition;
  (a9) from 9% to 14% by weight the total composition;
  (a10) from 10% to 14% by weight the total composition;
  (a11) from 9% to 13% by weight the total composition;
  (a12) from 10% to 12% by weight the total composition;
  (a13) from 10% to 11% by weight the total composition.

With respect to ingredient (c) noted above for example, the amount of sunflower lecithin that may be included in the final composition is based on a percent by weight of the total weight of the final composition described herein. The composition may comprise ingredient (c) for example, in concentrations as follows:
  (c1) from 1% to 20% by weight the total composition;
  (c2) from 2% to 19% by weight the total composition;
  (c3) from 3% to 18% by weight the total composition;
  (c4) from 4% to 17% by weight the total composition;
  (c5) from 4% to 16% by weight the total composition;
  (c6) from 4% to 15% by weight the total composition;
  (c7) from 4% to 14% by weight the total composition;
  (c8) from 4% to 13% by weight the total composition;
  (c9) from 4% to 12% by weight the total composition;
  (c10) from 4% to 11% by weight the total composition;
  (c11) from 5% to 10% by weight the total composition;
  (c12) from 6% to 9% by weight the total composition;
  (c13) from 6% to 8% by weight the total composition.

With respect to ingredient (a) noted above for example, the L-glutathione reduced may comprise a purity before it is included in the composition in percentages as follows:
  (aa1) from 97% to 99.9% purity;
  (aa2) from 97.5% to 99.9% purity;
  (aa3) from 98% to 99.9% purity;
  (aa4) from 98.5% to 99.9% purity;
  (aa5) from 99% to 99.9% purity;
  (aa6) from 99.1% to 99.9% purity;
  (aa7) from 99.2% to 99.9% purity;
  (aa8) from 99.3% to 99.9% purity;
  (aa9) from 99.4% to 99.9% purity;
  (aa10) from 99.5% to 99.9% purity;
  (aa11) from 99.6% to 99.9% purity;
  (aa12) from 99.7% to 99.9% purity;
  (aa13) from 99.8% to 99.9% purity.

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, and so forth.

Also, according to one or more non-limiting embodiments of the disclosure, any of the concentrations for ingredients (a) or (c), for example, as listed above, may indicate the concentration for any of ingredients (b) and (d) thru (h), as listed above. For example, an embodiment of the disclosure may comprise, for example, (a7) from 8% to 14% by weigh the total composition of L-glutathione reduced, and equal parts by weight of lemon essential oil and peppermint essential oil. For example, the composition may comprise all, or any combination of but not all, of the ingredients (a) thru (h).

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations might be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A composition for reducing oxidative stress in a user, the composition comprising:
    an effective amount of reduced glutathione for reducing oxidative stress in the user; and
    a deoxygenated water solvent;
    wherein the composition is encapsulated in a phospholipid liposome structure; and
    wherein the composition is packaged in an airless dispenser configured to maintain an anaerobic environment.

2. The composition of claim 1, wherein the phospholipid liposome structure is plant-based, and wherein the composition further comprises one or more of sunflower lecithin, an essential oil, *stevia* extract, sodium benzoate, or potassium sorbate.

3. The composition of claim 1, wherein the reduced glutathione comprises from 8% to 14% by weight of the total composition.

4. The composition of claim 1, where the composition comprises from 500 mg to 600 mg reduced glutathione per 4 g of the composition.

5. The composition of claim 1, wherein the reduced glutathione comprises a purity from 98% to 99.9% purity.

6. The composition of claim 1, further comprising an effective amount of one or more preservatives selected from a list comprising: potassium sorbate, sodium benzoate, sorbic acid, benzoic acid, natural benzyl alcohol, erythorbic acid, sodium erythorbate, ferrous gluconate, methyl paraben, potassium benzoate, rosemary extract, and sodium citrate.

7. The composition of claim 1, further comprising an effective amount of one or more natural flavoring components for improving an overall flavor of the composition selected from a list comprising: lemon essential oil, peppermint essential oil, monk fruit extract, agave, honey, natural cane sugar, glucose, fruit concentrate, natural fruit powder, spearmint essential oil, wintergreen essential oil, orange essential oil, tangerine essential oil, lavender essential oil, and *stevia* extract.

8. The composition of claim 1, wherein the composition is prepared for liquid oral consumption.

9. The composition of claim 1, wherein the composition is prepared for topical application.

10. The composition of claim 1, wherein the composition is prepared for intravenous or intramuscular administration.

11. The composition of claim 1, wherein the composition comprises from 4 g to 20 g reduced glutathione per 100 mL of the deoxygenated water solvent.

12. A method of reducing oxidative stress in a user, comprising:
    providing the composition according to claim 1 to the user, wherein the composition comprises:
    an effective amount of reduced glutathione for reducing oxidative stress in the user; and
    a deoxygenated water solvent.

13. The method of claim 12, wherein the reduced glutathione comprises from 8% to 14% by weight of the total composition.

14. The method of claim 12, wherein the composition comprises from 500 mg to 600 mg reduced glutathione per 4 g of the composition.

15. The method of claim 12, wherein the reduced glutathione comprises a purity from 98% to 99.9% purity.

16. The method of claim 12, wherein the reduced glutathione comprises a purity from 99.0% to 99.9% purity.

17. The method of claim 12, wherein the composition further comprises an effective amount of one or more preservatives selected from a list comprising: potassium sorbate, sodium benzoate, sorbic acid, benzoic acid, natural benzyl alcohol, erythorbic acid, sodium erythorbate, ferrous gluconate, methyl paraben, potassium benzoate, rosemary extract, and sodium citrate.

18. The method of claim 12, wherein the composition further comprises an effective amount of one or more natural flavoring components for improving an overall flavor of the composition selected from a list comprising: lemon essential oil, peppermint essential oil, monk fruit extract, agave, honey, natural cane sugar, glucose, fruit concentrate, natural fruit powder, spearmint essential oil, wintergreen essential oil, orange essential oil, tangerine essential oil, lavender essential oil, and *stevia* extract.

19. The method of claim 12, wherein the composition is provided to the user for liquid oral consumption.

20. The method of claim 12, wherein the composition is provided to the user for topical administration.

21. The method of claim 12, wherein the composition is provided to the user for intravenous or intramuscular administration.

22. The method of claim 12, wherein the composition comprises from 4 g to 20 g reduced glutathione per 100 mL of the deoxygenated water solvent.

23. The method of claim 12, wherein the composition increases blood-serum levels of reduced glutathione in the user by at least 25%.

* * * * *